(12) United States Patent
Fennessy et al.

(10) Patent No.: US 11,241,241 B2
(45) Date of Patent: Feb. 8, 2022

(54) SURGICAL BLADE ASSEMBLY

(71) Applicant: Stryker European Holdings I, LLC, Kalamazoo, MI (US)

(72) Inventors: Colin Fennessy, Ratoath (IE); Colin Stanley, Kilmacthomas (IE); Conor Mac An Tuile, Muine Bheag (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 310 days.

(21) Appl. No.: 16/403,961

(22) Filed: May 6, 2019

(65) Prior Publication Data

US 2019/0343537 A1 Nov. 14, 2019

Related U.S. Application Data

(60) Provisional application No. 62/670,158, filed on May 11, 2018.

(51) Int. Cl.
*A61B 17/14* (2006.01)
*A61L 31/02* (2006.01)
*A61B 17/00* (2006.01)

(52) U.S. Cl.
CPC .......... *A61B 17/144* (2016.11); *A61L 31/022* (2013.01); *A61B 2017/00473* (2013.01)

(58) Field of Classification Search
CPC ...... A61B 17/14; A61B 17/144; B23D 51/08; B23D 51/10
See application file for complete search history.

(56) References Cited

U.S. PATENT DOCUMENTS

| 3,964,163 A | * | 6/1976 | Russo | B23D 51/10 |
| | | | | 30/166.3 |
| 4,617,930 A | | 10/1986 | Saunders | |
| 5,201,749 A | * | 4/1993 | Sachse | B23D 49/165 |
| | | | | 30/393 |
| 6,871,405 B2 | | 3/2005 | Reale et al. | |
| 7,744,616 B2 | | 6/2010 | O'Donoghue | |
| 9,566,074 B2 | | 2/2017 | Milburn et al. | |
| 2012/0041443 A1 | | 2/2012 | Landon | |

FOREIGN PATENT DOCUMENTS

| WO | 2017106533 A2 | 6/2017 |
| WO | 2017180493 A1 | 10/2017 |

* cited by examiner

*Primary Examiner* — Andrew Yang
(74) *Attorney, Agent, or Firm* — Howard & Howard Attorneys PLLC

(57) ABSTRACT

A surgical blade assembly includes a blade having side surfaces defining a width greater than its thickness. The surgical blade assembly also includes a reinforcing member having a body portion, and first and second arms extending from the body portion to define a receiving portion. The receiving portion is configured to receive the blade and the first and second arms are configured to abut the side surfaces of the blade. The first and second arms act as a strut to reinforce the blade against external forces applied to the blade. The blade and the reinforcing member may include coupling features to prevent separation of the reinforcing member from the blade. The blade and the reinforcing member may be substantially perpendicular to each other when coupled.

20 Claims, 13 Drawing Sheets

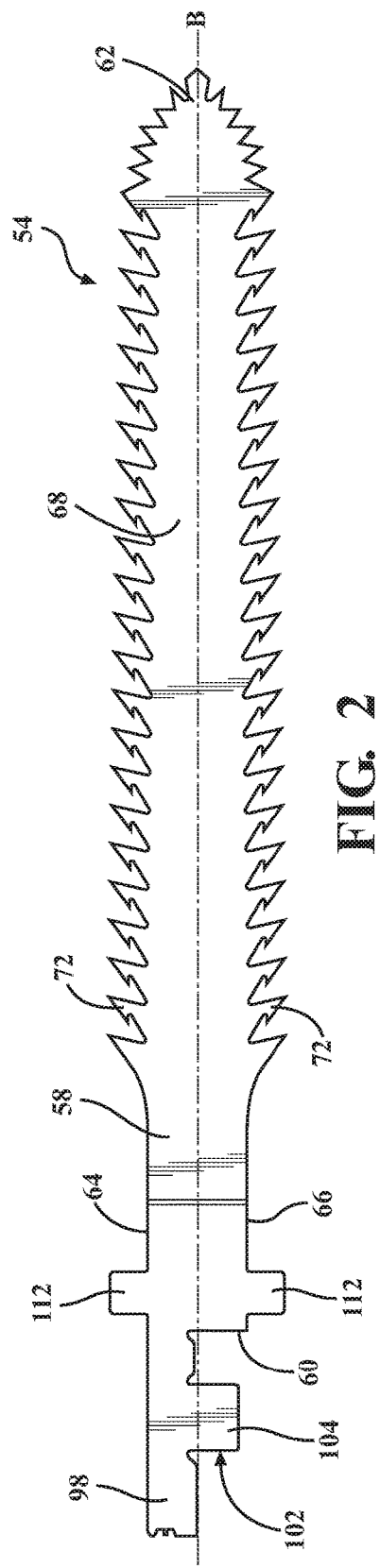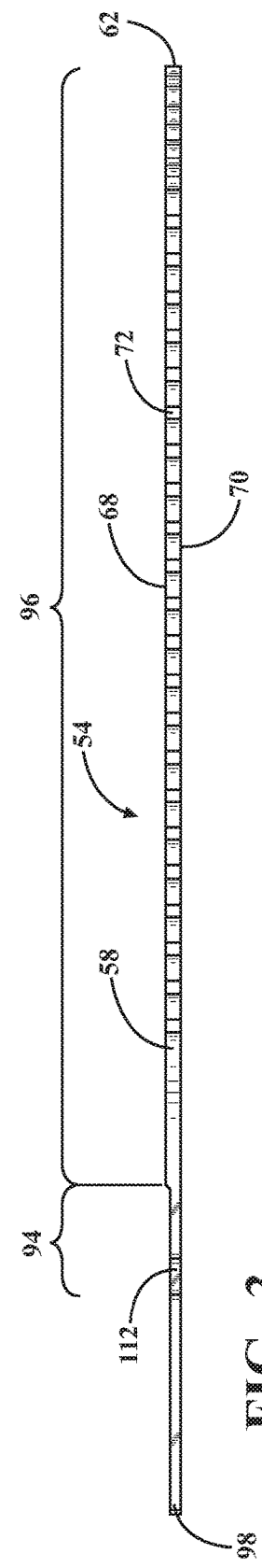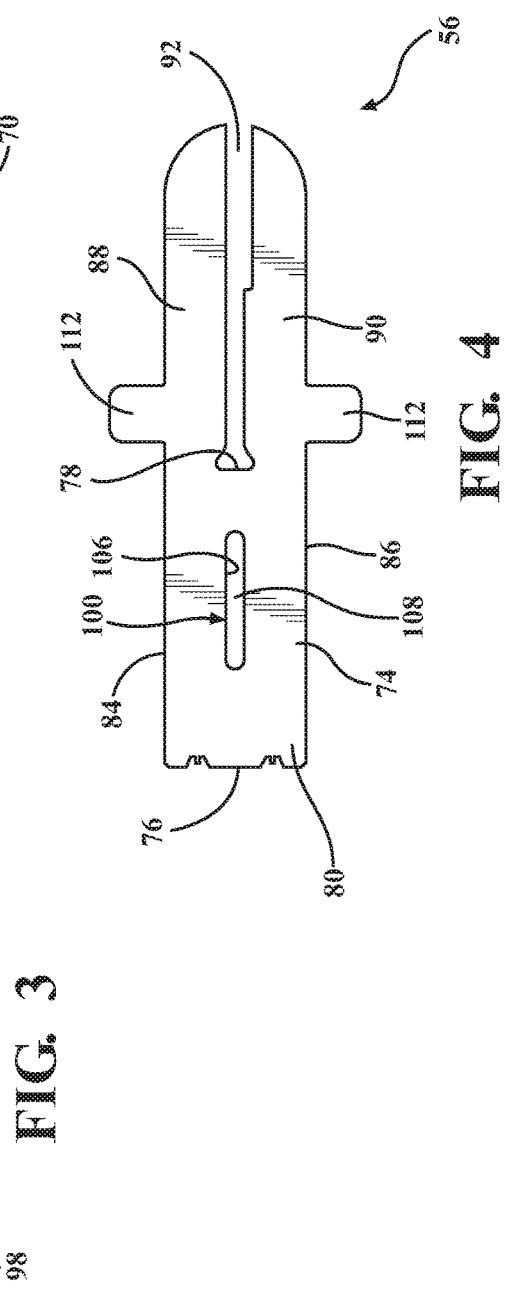
FIG. 2
FIG. 3
FIG. 4

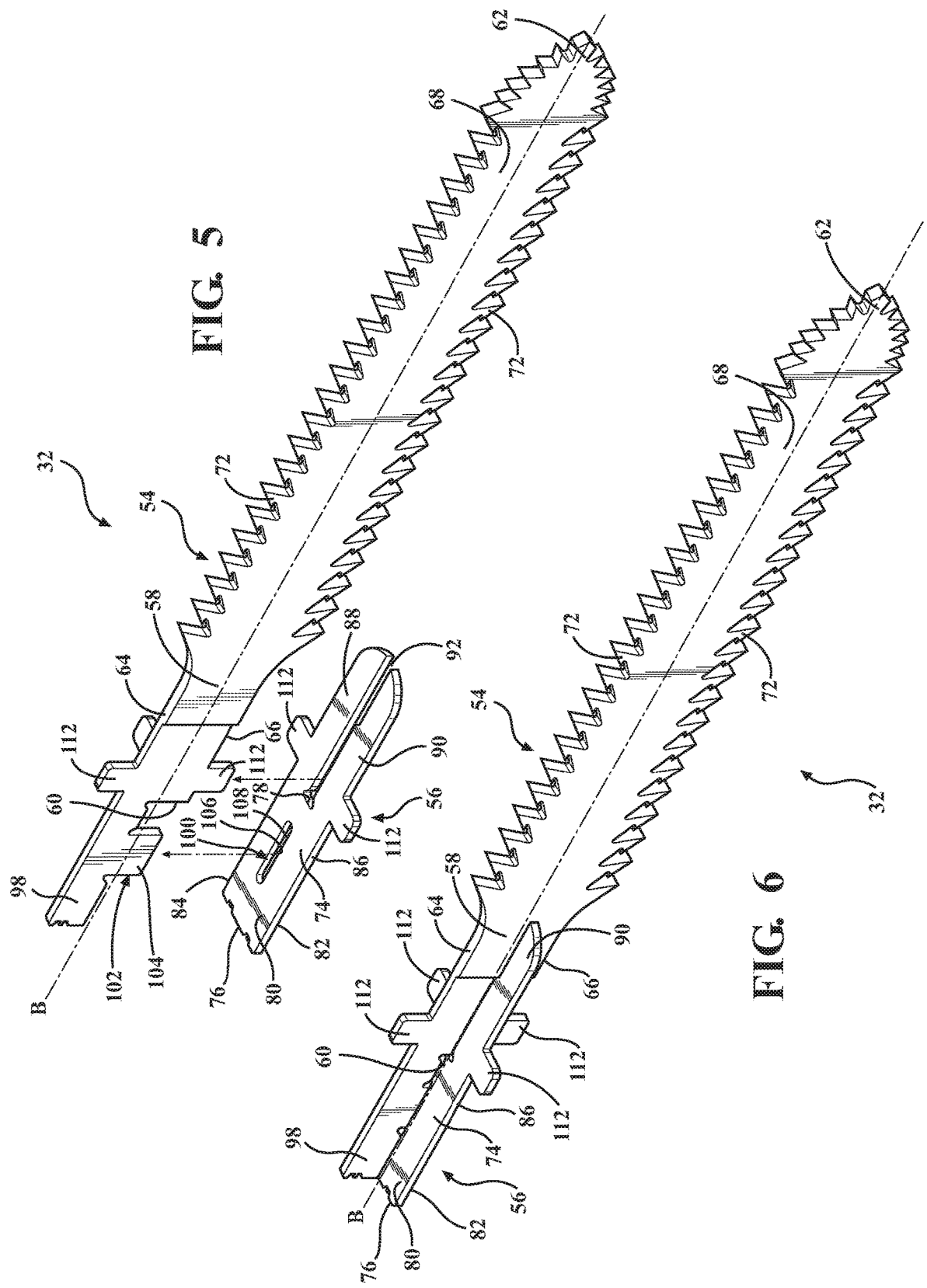

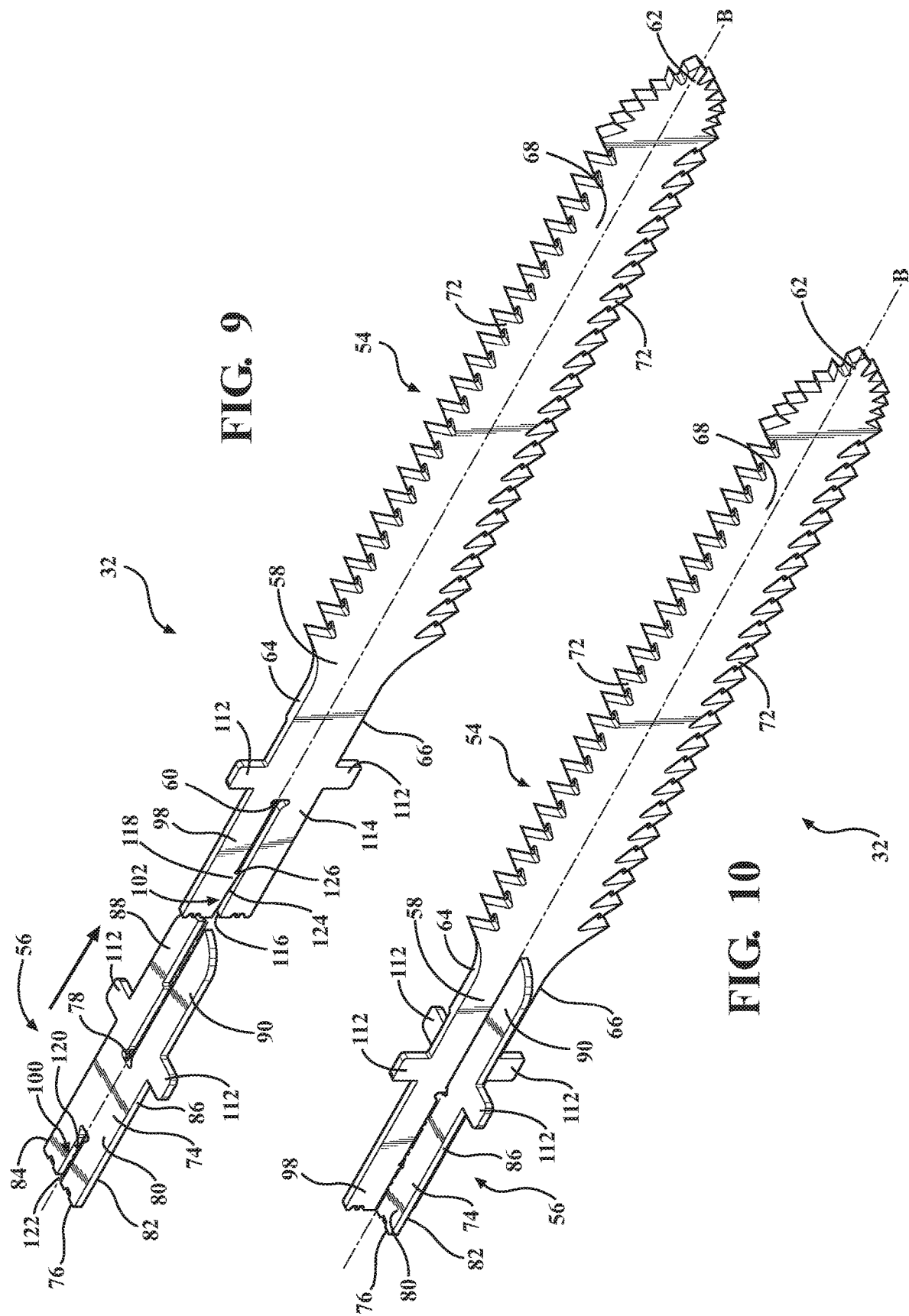

SURGICAL BLADE ASSEMBLY

CROSS-REFERENCE TO RELATED APPLICATIONS

This patent application claims priority to and all advantages of U.S. Provisional Patent Application No. 62/670,158 filed May 11, 2018, the entire contents of which are incorporated herein by reference.

TECHNICAL FIELD

The present disclosure is generally directed to surgical assemblies, and more specifically, surgical assemblies including surgical blades for cutting bone and other tissue.

BACKGROUND

In a surgical procedure it is sometimes necessary to use a saw to remove tissue, including bone and cartilage. Often a powered saw is used to perform this procedure. Attached to the saw is a blade. A drive assembly internal to the saw oscillates the blade in a back and forth motion. Some saws and blades are designed so that, when the saw is actuated, the blade moves back and forth along its longitudinal axis. This type of blade is known as a reciprocating saw blade. This type of blade is provided with teeth that extend outwardly from a blade body.

As the blade moves back and forth along its longitudinal axis, the blade is often subject to stress near a portion of the blade held by the saw. It is desired to reduce such stress in the blade for a given load condition.

BRIEF DESCRIPTION OF THE DRAWINGS

Advantages of the present disclosure will be readily appreciated as the same becomes better understood by reference to the following detailed description when considered in connection with the accompanying drawings.

FIG. 2 is an elevation view of an example blade of the surgical blade assembly.

FIG. 3 is a plan view of the blade of FIG. 2.

FIG. 4 is a plan view of an example reinforcing member of the surgical blade assembly.

FIG. 5 is a perspective exploded view of an example surgical blade assembly with the reinforcing member of FIG. 4 configured to be coupled to the blade of FIG. 2.

FIG. 6 is another perspective view of the surgical blade assembly of FIG. 5 with the reinforcing member coupled to the blade.

FIG. 9 is a perspective exploded view of another example of the surgical blade assembly with the reinforcing member of FIG. 8 configured to be coupled to the blade of FIG. 7.

FIG. 10 is another perspective view of the surgical blade assembly of FIG. 9 with the reinforcing member coupled to the blade.

DETAILED DESCRIPTION

Figure 1:
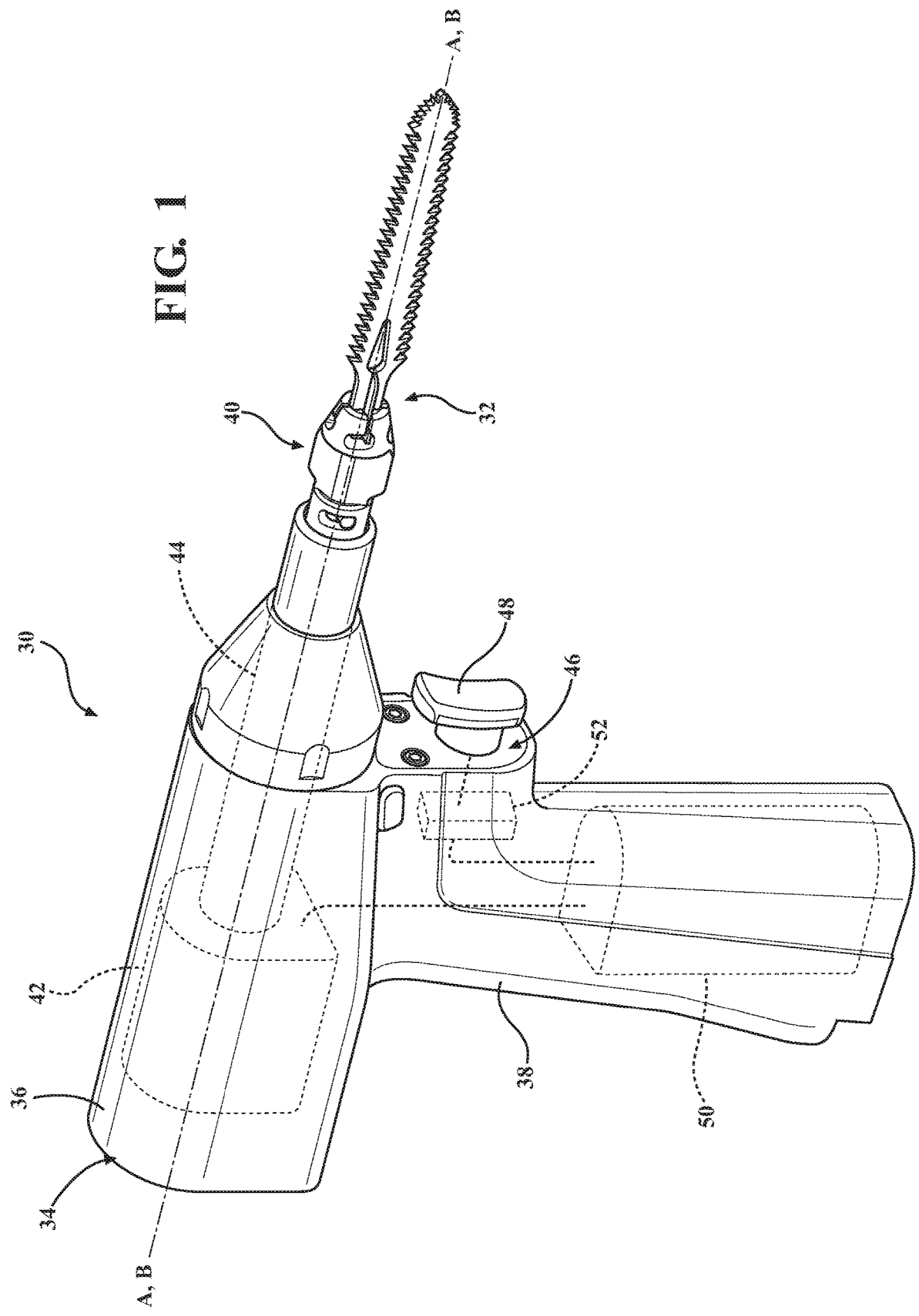
FIG. 1 is a perspective view of an example surgical saw including a surgical blade assembly having a blade and a reinforcing member.

A surgical blade assembly for a surgical saw includes a blade comprising a body portion has a proximal end, a distal end, and a length between the proximal and distal ends. The body portion has opposed top and bottom surfaces and opposed first and second side surfaces between the top and bottom surfaces. The blade has one or more teeth that extend outwardly from at least one of the top and bottom surfaces of the body portion. The surgical blade assembly also includes a reinforcing member comprising a body portion having a proximal end, a distal end, and a length that extends between the proximal and distal ends. The reinforcing member comprises a first arm extending from the distal end of the body portion of the reinforcing member and a second arm extending from the distal end of the body portion of the reinforcing member. The second arm is spaced from the first arm to define a receiving portion configured to receive the proximal end of the body portion of the blade. The first and second arms are configured to abut the first and second side surfaces of the body portion of the blade to act as a strut to reinforce the blade when the receiving portion receives the proximal end of the body portion of the blade.

The reinforcing member may comprise a first coupling feature, and the blade may comprise a second coupling feature. The first and second coupling features may be configured to engage each other when the receiving portion receives the proximal end of the body portion of the blade to prevent separation of the reinforcing member from the blade.

One of the first and second coupling features may comprise a projection. The other of the first and second coupling features may comprise a surface defining one of a void and a recess.

The blade may further comprise a leg extending from the proximal end of the body portion of the blade. The leg may be adjacent the body portion of the reinforcing member when the receiving portion receives the proximal end of the body portion of the blade.

The body portion of the reinforcing member may comprise the first coupling feature and the leg of the blade may comprise the second coupling feature.

The second coupling feature may comprise a projection extending from the leg. The first coupling feature may comprise a surface of the body portion of the reinforcing member defining a void to receive the projection when the receiving portion receives the proximal end of the body portion of the blade.

The leg may be further defined as a first leg. The blade may comprise a second leg extending from the proximal end of the body portion. The second leg may be spaced from the first leg to define a channel configured to receive the distal end of the body portion of the reinforcing member when the receiving portion receives the proximal end of the body portion of the blade.

The second coupling feature may comprise a projection extending from the first leg into the channel. The first coupling feature may comprise a surface of the reinforcing member that may define a void to receive the projection when the receiving portion receives the proximal end of the body portion of the blade.

The projection may have a ramped portion to permit the channel to receive the distal end of the reinforcing member. The projection may have a stepped portion configured to abut the surface of the reinforcing member defining the void to prevent the reinforcing member from being separated from the blade when the receiving portion receives the proximal end of the body portion of the blade.

At least one of the blade and the reinforcing member may comprise a mount feature to releasably attach at least one of the blade and the reinforcing member to the surgical saw.

The mount feature may comprise a protrusion extending outwardly from at least one of the leg, the body portion of the blade, the first arm, the second arm, and the body portion of the reinforcing member.

The body portion of the blade may have a distal region connecting the top surface and the bottom surface. The distal region may be disposed between the first and second side surfaces. The blade may have one or more teeth that extend outwardly from the distal region of the body portion of the blade, with the one or more teeth that extend outwardly from the distal region of the body portion of the blade being configured to permit plunge cutting.

The length of the body portion of the blade may extend along an axis. At least one of the one or more teeth that extend outwardly from the distal region of the body portion of the blade may extend in a direction substantially aligned with the axis.

The length of the body portion of the blade may extend along an axis. At least one of the one or more teeth that extend outwardly from the distal region of the body portion of the blade may have a tooth face defining a face plane and a tooth back that may define a back plane intersecting the face plane. At least one of the one or more teeth that extend outwardly from the distal region of the body portion of the blade may define a reference plane bisecting the face and back planes, with the reference plane and the axis creating an angle relative to each other that is less than thirty degrees.

The blade and the reinforcing member may be perpendicular to each other when the receiving portion receives the proximal end of the body portion of the blade.

The body portion of the blade may have a first region adjacent the proximal end of the body portion of the blade. The body portion of the blade may have a second region adjacent the first region. The opposed side surfaces may define a first thickness at the first region of the body portion of the blade and a second thickness larger than the first thickness at the second region of the body portion of the blade.

The receiving portion may be adapted to accommodate the second thickness of the body portion of the blade such that the first and second arms abut the first and second side surfaces of the body portion of the blade at the second region of the body portion of the blade when the receiving portion receives the proximal end of the body portion of the blade.

At least one of the blade and the reinforcing member may comprise stainless steel.

At least one of the blade and the reinforcing member may comprise martensitic stainless steel.

At least one or more teeth may extend outwardly from the body portion of the blade such that the one or more teeth are coplanar with the body portion of the blade.

The blade may be formed by laser cutting.

A blade has a proximal end, a distal end, and a length that extends between the proximal and distal end. A reinforcing member is provided for reinforcing the blade. At least a portion of one of the reinforcing member and the blade is inserted into the other of the reinforcing member and the blade. The reinforcing member is coupled mechanically to the blade without materially altering the physical properties of at least one of the reinforcing member and the blade.

A surgical blade assembly includes a blade comprising a body portion having a proximal end, a distal end, and a length between the proximal and distal ends. The body portion has opposed top and bottom surfaces and opposed first and second side surfaces between the top and bottom surfaces. The first and second side surfaces are substantially parallel and define a thickness therebetween. The blade has one or more teeth that extend outwardly from at least one of the top and bottom surfaces of the body portion. The surgical blade assembly further includes a reinforcing member comprising a body portion having a proximal end, a distal end, and a length that extends between the proximal and distal ends. The body portion of the reinforcing member has opposed top and bottom surfaces being substantially parallel and defining a thickness therebetween. The body portion of the reinforcing member is coupled to the body portion of the blade such that the thickness of the body portion of the reinforcing member, i.e., the top and bottom surfaces of the reinforcing member, and the thickness of the body portion of the blade, i.e., the first and second side surfaces of the body portion of the blade, are substantially perpendicular to each other. The reinforcing member is coupled to at least one of the first and second side surfaces of the body portion of the blade to act as a strut to reinforce the blade.

A method of coupling a surgical blade assembly to a surgical saw including a saw chuck assembly, the method comprising providing the surgical blade assembly, and the method further comprising providing a blade and a reinforcing member of the surgical blade assembly. The blade provided comprises a body portion having a proximal end, a distal end, and a length between the proximal and distal ends, with the body portion having opposed first and second side surfaces. The reinforcing member provided comprises a body portion having a proximal end, a distal end, and a length that extends between the proximal and distal ends. The reinforcing member provided comprises a first arm extending from the distal end of the body portion of the reinforcing member and a second arm extending from the distal end of the body portion of the reinforcing member and being spaced from the first arm to define a receiving portion. The reinforcing member provided is coupled to the blade such that the receiving portion of the reinforcing member receives the proximal end of the blade and the first and second arms abut the first and second side surfaces of the body portion of the blade to act as a strut to reinforce the blade. The reinforcing member and the blade are coupled to the saw chuck assembly such that a portion of each of the blade and the reinforcing member are received within the saw chuck assembly.

The method of coupling may further comprise orienting the body portion of the blade perpendicular relative to the body portion of the reinforcing member prior to coupling the reinforcing member to the blade.

FIG. 1 shows a surgical saw 30 including a surgical blade assembly 32 in accordance with an example of the present disclosure. The surgical saw 30 comprises a saw housing 34. In one configuration, the saw housing 34 includes a barrel 36 and a handgrip 38 extending from the barrel 36. The surgical saw 30 further comprises a saw chuck assembly 40 coupled to the barrel 36 of the saw housing 34. The surgical blade assembly 32 is configured to be releasably coupled to the saw chuck assembly 40.

The barrel 36 defines an interior of a portion of the housing 34. A motor 42, shown schematically in FIG. 1, is disposed within the interior of the barrel 36. A transmission 44, also shown schematically in FIG. 1, is disposed within the interior of the barrel 36 and operatively coupled to the motor 42 and the saw chuck assembly 40. In one configuration, the motor 42 is a DC motor. A battery (not shown) is attached to the handgrip 38. The battery supplies current for energization of the motor 42.

A trigger assembly 46 is coupled to the handgrip 38 and includes a trigger 48 movable relative to the handgrip 38. The trigger 48 is operable from a first position projecting away from the handgrip 38 to a second position inward of the first position. The trigger 48 may be operable in one or more intermediate positions between the first position and the second position. A user may grasp the handgrip 38 and depress the trigger 48 toward the second position and a biasing mechanism (not shown) such as a spring may bias the trigger 48 toward the first position.

Internal to the handgrip 38 is a control module 50, shown schematically in FIG. 1, coupled to the motor 42 and the battery. The control module 50 includes one or more sensors 52 that generate one or more energization signals responsive to actuation of the trigger 48. The motor 42 is configured to receive the energization signals and generate rotational energy. The transmission 44 is configured to convert rotational energy from the motor 42 to reciprocal movement of the saw chuck assembly 40 along an axis A, and thus reciprocal movement of the surgical blade assembly 32 parallel to the axis A when the surgical blade assembly 32 is coupled to the saw chuck assembly 40. More specifically, the reciprocal movement of the saw chuck assembly 40 and the surgical blade assembly 32 is a back and forth movement along the axis A.

FIG. 1 shows the barrel 36 and the handgrip 38 arranged in a pistol configuration with the handgrip 38 substantially oriented perpendicularly from the barrel 36. The user may grasp the handgrip 38 with one or both hands, and may further support the barrel 36 with the other hand. In another configuration, the handgrip 38 is integrated with the barrel 36 (e.g., the handgrip 38 is removed to define a substantially cylindrical housing) such that the user may grasp the barrel 36 with one or both hands to operate the surgical saw 30. In other configurations, the surgical saw 30 has alternative structure to enable operation of the surgical saw 30 to provide reciprocal motion to the saw chuck assembly 40 and the surgical blade assembly 32 when the surgical blade assembly 32 is coupled to the saw chuck assembly 40.

As shown in FIGS. 2-6, one example of the surgical blade assembly 32 is illustrated. The surgical blade assembly 32 comprises a blade 54 (shown in FIG. 2) and a reinforcing member 56 (shown in FIG. 4) configured to be coupled to the blade 54. The blade 54 includes a body portion 58 having a proximal end 60, a distal end 62, and a length defined between the proximal and distal ends 60, 62. The length extends along a blade axis B that is parallel to the axis A such that the saw chuck assembly 40 reciprocates along the blade axis B. In the illustrated configurations, referring back to FIG. 1, the blade axis B is collinear to the axis A such that the saw chuck assembly 40 reciprocates along the axis A and the blade axis B.

As shown in FIGS. 2 and 3, the body portion 58 of the blade 54 has opposed top and bottom surfaces 64, 66 defining a blade width and opposed first and second side surfaces 68, 70 between the top and bottom surfaces 64, 66 defining a blade thickness. The blade width is greater than the blade thickness. In one configuration the blade width is six or more times larger than the blade thickness. In other configurations the blade width is between two and six times larger than the blade thickness. In some configurations the blade thickness is uniform along the length of the body portion 58 of the blade 54. In other configurations, the blade thickness changes along the length of the body portion 58 of the blade 54.

The blade 54 also has one or more teeth 72 that extend outwardly from at least one of the top and bottom surfaces 64, 66 of the body portion 58 of the blade 54. In the configurations shown in the figures, the blade 54 has a plurality of teeth 72 that extend outwardly from both the top and bottom surfaces 64, 66 of the body portion 58 of the blade 54.

As shown in FIG. 4, the reinforcing member 56 includes a body portion 74 having a proximal end 76, a distal end 78, and a length that extends between the proximal and distal ends 76, 78. The reinforcing member 56 has opposed top and bottom surfaces 80, 82 (bottom surface 82 is shown in FIGS. 5 and 6) defining a reinforcing member thickness and opposed first and second side surfaces 84, 86 between the top and bottom surfaces 80, 82 defining a reinforcing member width. The reinforcing member width is greater than the reinforcing member thickness. In one configuration the reinforcing member width is six or more times larger than the reinforcing member thickness. In other configurations the reinforcing member width is between two and six times larger than the reinforcing member thickness.

The reinforcing member 56 includes a first arm 88 extending from the distal end 78 of the body portion 74 of the reinforcing member 56 and a second arm 90 extending from the distal end 78 of the body portion 74 of the reinforcing member 56. The second arm 90 is spaced from the first arm 88 to define a receiving portion 92 configured to receive the proximal end 60 of the body portion 58 of the blade 54. A proximal end of the receiving portion 92 may define the distal end 78 of the body portion 74, as illustrated in FIG. 6. In other words, the body portion 74 of the reinforcing member 56 may be a portion of the reinforcing member 56 defined between the proximal end 76 of the body portion 74 and the proximal end of the receiving portion 92.

The first and second arms 88, 90 act as a strut to reinforce the body portion 58 of the blade 54 when the receiving portion 92 receives the proximal end 60 of the body portion 58 of the blade 54. As the blade width is larger than the blade thickness, the first and second arms 88, 90 mitigate deflection of the body portion 58 of the blade 54 that may otherwise occur normal to the first and second side surfaces 68, 70 of the body portion 58 of the blade 54 during reciprocation of the surgical blade assembly 32. In other words, the first and second arms 88, 90 of the reinforcing member 56 reduce the stress associated with whip during operation of the surgical saw 30. The mitigation of deflection of the body portion 58 further reduces stresses associated with external forces applied to the blade 54, for example, from bony anatomy during reciprocation of the surgical blade assembly 32 with the bony anatomy.

In one configuration, as shown in FIG. 5, the first and second arms 88, 90 are coplanar in thickness with the body portion 74 of the reinforcing member 56. In other configurations, the first and second arms 88, 90 are thicker than the body portion 74 of the reinforcing member 56. In still other configurations, the first and second arms 88, 90 are thinner than the body portion 74 of the reinforcing member 56.

As mentioned, the reinforcing member 56 acts as a strut to the blade 54 in a direction normal the thickness. This means that contact between the blade 54 and the reinforcing member 56 occurs when the blade 54 is deflected. However, it may or may not include contact between the blade 54 and the reinforcing member 56 when the blade 54 is deflected by less than certain amounts. In the configuration shown in FIGS. 5 and 6, the first and second arms 88, 90 are spaced apart from one another such that the distance between approximates the thickness of the body portion 58 of the blade 54 so that the first and second arms 88, 90 abut the first and second side surfaces 68, 70 of the body portion 58 of the blade 54 when the receiving portion 92 receives the proximal end 60 of the body portion 58 of the blade 54. In other configurations, the first and second arms 88, 90 are spaced apart from one another such that the first and second arms 88, 90 extend adjacent to but do not directly contact at least one of the first and second side surfaces 68, 70 of the body portion 58 of the blade 54 when the receiving portion 92 receives the proximal end 60 of the body portion 58 of the blade 54. In this configuration, the space between at least one of the first and second arms 88, 90 and the body portion 58 of the blade 54 when the receiving portion 92 receives the proximal end 60 of the body portion 58 of the blade 54 is less than the anticipated deflection of the blade 54 during operation (e.g. less than 0.5 mm) for mitigating deflection of the body portion 58 of the blade 54 during reciprocation of the surgical blade assembly 32.

In the illustrated configurations, the blade 54 and the reinforcing member 56 are perpendicular to each other when the receiving portion 92 receives the proximal end 60 of the body portion 58 of the blade 54. More specifically, the blade thickness and the reinforcing member thickness are perpendicular to each other when the receiving portion 92 receives the proximal end 60 of the body portion 58 of the blade 54. In other configurations, the blade 54 and the reinforcing member 56 are not perpendicular to each other when the receiving portion 92 receives the proximal end 60 of the body portion 58 of the blade 54 such that the blade 54 and reinforcing member 56 form oblique angles relative to each other when the receiving portion 92 receives the proximal end 60 of the body portion 58 of the blade 54.

In some configurations, as shown in FIG. 3, the body portion 58 of the blade 54 has a first region 94 adjacent the proximal end 60 of the body portion 58 of the blade 54 and a second region 96 adjacent the first region 94 between the first region 94 and the distal end 62 of the body portion 58 of the blade 54. The opposed side surfaces 68, 70 of the body portion 58 of the blade 54 define a first thickness at the first region 94 and a second thickness larger than the first thickness at the second region 96.

As shown in FIGS. 5 and 6, the receiving portion 92 is adapted to accommodate the second thickness of the body portion 58 of the blade 54 such that the first and second arms 88, 90 abut the first and second side surfaces 68, 70 of the body portion 58 of the blade 54 at the second region 96 of the body portion 58 of the blade 54 when the receiving portion 92 receives the proximal end 60 of the body portion 58 of the blade 54.

In the configuration shown in FIGS. 5 and 6, the receiving portion 92 is adapted to accommodate both the first and second thicknesses of the body portion 58 of the blade 54 such that the first and second arms 88, 90 abut the first and second side surfaces 68, 70 of the body portion 58 of the blade 54 at the first and second regions 94, 96 of the body portion 58 of the blade 54 when the receiving portion 92 receives the proximal end 60 of the body portion 58 of the blade 54. In other configurations, the receiving portion 92 is adapted to accommodate both the first and second thicknesses of the body portion 58 of the blade 54 such that the first and second arms 88, 90 abut the first and second side surfaces 68, 70 of the body portion 58 of the blade 54 only at the second region 96 of the body portion 58 of the blade 54 when the receiving portion 92 receives the proximal end 60 of the body portion 58 of the blade 54. In still other configurations, the receiving portion 92 is adapted accommodate the first thickness of the body portion 58 of the blade 54 such that the first and second arms 88, 90 abut the first and second side surfaces 68, 70 of the body portion 58 of the blade 54 only at the first region 94 of the body portion 58 of the blade 54.

In some configurations, as shown in FIGS. 2 and 4, the blade 54 further includes a leg 98 extending from the proximal end 60 of the body portion 58 of the blade 54. The leg 98 is configured to be adjacent the body portion 74 of the reinforcing member 56 when the receiving portion 92 receives the proximal end 60 of the body portion 58 of the blade 54.

In one configuration, as shown in FIG. 5, the leg 98 is coplanar in thickness with the body portion 58 of the blade 54. In other configurations, the leg 98 is thicker than the body portion 58 of the blade 54. In still other configurations, the leg 98 is thinner than the body portion 58 of the blade 54.

In some configurations, as shown in FIGS. 2 and 4, the reinforcing member 56 includes a first coupling feature 100 and the blade 54 includes a second coupling feature 102. The first and second coupling features 100, 102 are configured to engage each other when the receiving portion 92 receives the proximal end 60 of the body portion 58 of the blade 54 to prevent separation of the reinforcing member 56 from the blade 54. In the configurations shown, the body portion 74 of the reinforcing member 56 includes the first coupling feature 100, and the leg 98 of the blade 54 includes the second coupling feature 102.

In the configuration shown in FIGS. 2 and 4, the second coupling feature 102 includes a projection 104 extending from the leg 98, and the first coupling feature 100 has a surface 106 of the body portion 74 of the reinforcing member 56 defining a void 108 for receiving the projection 104. Referring to FIG. 4, the surface 106 has a continuous perimeter to define the void 108.

In other configurations, one of the first and second arms 88, 90 of the reinforcing member 56 may include the first coupling feature 100 and the body portion 58 of the blade 54 includes the second coupling feature 102. In such a configuration, the first coupling feature 100 may include a projection extending from the body portion 74 or first and second arms 88, 90 of the reinforcing member 56 and the second coupling feature 102 has a surface of the body portion 58 or leg 98 of the blade 54 defining a void for receiving the projection. In still other configurations, the surface 106 may define a recess for receiving the projection 104.

As shown in FIG. 5, the reinforcing member 56 is coupled to the blade 54 by aligning the receiving portion 92 of the reinforcing member 56 with the proximal end 60 of the body portion 58 of the blade 54 and pressing the reinforcing member 56 and the blade 54 together. In one configuration the reinforcing member 56 and the blade 54 are pressed using a pneumatic press. In other configurations, the reinforcing member 56 and the blade 54 are pressed together in another manner known in the art. In the configuration shown in FIG. 5, the reinforcing member 56 and blade 54 are pressed together in a direction transverse to the blade axis B. In alternative configurations to be described, the reinforcing member 56 and blade 54 are pressed together in a direction parallel to the blade axis B. The receiving portion 92 receives the proximal end 60 of the body portion 58 of the blade 54 and the void 108 receives the projection 104.

In some configurations, the projection 104 is tapered such that at least one of a width and a thickness of the projection 104 is thicker proximal the leg 98 and thinner distal the leg 98 such that as the void 108 receives the projection 104, the projection 104 and surface 106 of the body portion 74 of the reinforcing member 56 abut to provide an interference fit to couple the reinforcing member 56 to the blade 54.

One of the blade 54 and the reinforcing member 56 may include one or more mount features to releasably couple at least one of the blade 54 and the reinforcing member 56 to the saw chuck assembly 40. In some configurations, the mount feature includes a protrusion 112 extending outwardly from at least one of the leg 98, the body portion 58 of the blade 54, the first arm 88, the second arm 90, and the body portion 74 of the reinforcing member 56. The protrusion 112 is releasably secured by the saw chuck assembly 40 to releasably couple the surgical blade assembly 32 to the saw chuck assembly 40 and thus reciprocate the surgical blade assembly 32 during operation of the surgical saw 30. In many configurations, the body portion 74 of the reinforcing member 56 and the body portion 58 of the blade 54 each include two opposing protrusions 112 extending away from their respective bodies and each other. In this manner, the saw chuck assembly 40 is configured to be releasably coupled to the surgical blade assembly 32 at four locations arranged about the blade axis B with the protrusions 112 oriented ninety degrees apart from one another. In alternative configurations, the surgical blade assembly 32 includes three or fewer protrusions 112 arranged about the blade axis B. In other configurations, the surgical blade assembly 32 includes five or more protrusions 112 arranged about the blade axis B. The reinforcing member 56 of the present disclosure advantageously provides structural support to the blade 54 as well as facilitate improved mounting to the saw chuck assembly 40. More specifically, portions of the both the blade 54 and the reinforcing member 56 may be disposed internal to the saw chuck assembly 40 when mounting the surgical blade assembly 32 to the saw chuck assembly 40.

Figure 7:
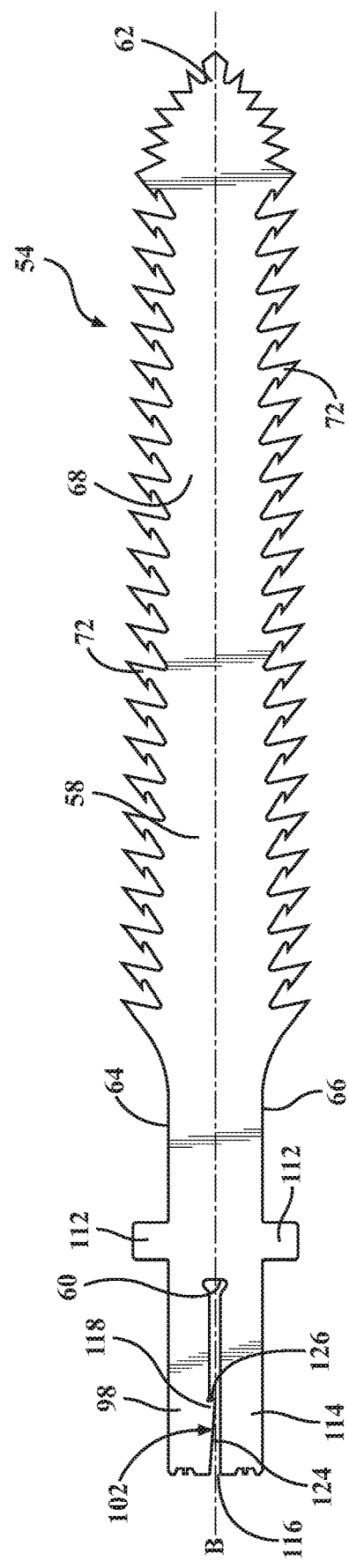
FIG. 7 is an elevation view of another example of a blade of the surgical blade assembly.
Figure 8:
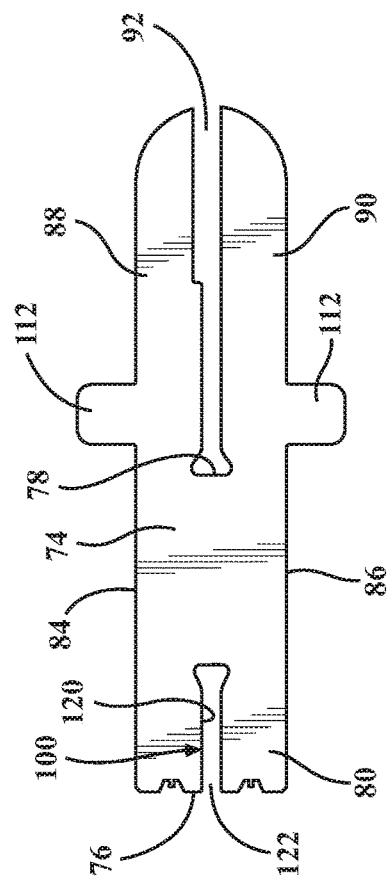
FIG. 8 is a plan view of another example of a reinforcing member of the surgical blade assembly.

FIGS. 7-10 show the surgical blade assembly 32 in accordance with another example of the present disclosure. In at least some respects the example shown in FIGS. 7-10 is the same as the example previously described with like numbers indicating like components. As shown in FIGS. 7-10, the leg 98 is further defined as a first leg 98 and the blade 54 includes a second leg 114 extending from the proximal end 60 of the body portion 58 of the blade 54 and being spaced from the first leg 98 to define a channel 116 configured to receive the distal end 78 of the body portion 74 of the reinforcing member 56 when the receiving portion 92 correspondingly receives the proximal end 60 of the body portion 58 of the blade 54. As shown in FIGS. 8 and 9, the first and second legs 98, 114 are spaced apart from one another such that the distance between approximates the thickness of the body portion 74 of the reinforcing member 56 so that the first and second legs 98, 114 abut the top and bottom surfaces 80, 82 of the body portion 74 of the reinforcing member 56 when the channel 116 receives the distal end 78 of the body portion 74 of the reinforcing member 56.

As shown in FIGS. 7 and 8, the second coupling feature 102 comprises a projection 118 extending from the first leg 98 into the channel 116. In other words, the channel 116 may be at least partially defined by the first leg 98, the second leg 114, and the projection 118. The first coupling feature 100 includes a surface 120 of the body portion 74 of the reinforcing member 56 defining a void 122 to receive the projection 118 when the receiving portion 92 receives the proximal end of the body portion 58 of the blade 54. In this configuration, the surface 120 does not have a continuous perimeter defining the void 122. In alternative configurations, the surface 120 has a continuous perimeter. In other configurations the surface 120 defines a recess such that the surface 120 does not extend between the top and bottom surfaces 80, 82 of the reinforcing member 56.

As shown in FIG. 7, the projection 118 has a ramped portion 124 to assist the channel 116 to receive the distal end 78 of the body portion 74 of the reinforcing member 56. The projection 118 has a stepped portion 126 configured to abut the surface 120 of the body portion 74 of the reinforcing member 56 that defines the void 122. Engagement between the projection 118 and the surface 120 defining the void 122 prevents the reinforcing member 56 from being separated from the blade 54 when the receiving portion 92 receives the proximal end 60 of the body portion 58 of the blade 54. In particular, as shown in FIG. 9, the reinforcing member 56 is coupled to the blade 54 by aligning the receiving portion 92 of the reinforcing member 56 with the channel 116 of the blade 54 and pressing the reinforcing member 56 and the blade 54 together. As the receiving portion 92 receives the proximal end 60 of the body portion 58 of the blade 54 and the channel 116 receives the body portion 74 of the reinforcing member 56, the ramped portion 124 of the projection 118 abuts the body portion 74 of the reinforcing member 56 to deflect one or both of the first and second legs 98, 114 to create enough space to accommodate the body portion 74 of the reinforcing member 56. Once the reinforcing member 56 and blade 54 have been pressed far enough for the void 122 to receive the projection 118, one or both of the first and second legs 98, 114 resiliently return to an original state with the projection 118 disposed with the void 122. The abutting surfaces of the stepped portion 126 of the projection 118 and the surface 120 prevents separation of the reinforcing member 56 from the blade 54. This feature maintains relative axial position between the blade 54 and the reinforcing member 56 and improves handling of the surgical blade assembly 32 without concern for the surgical blade assembly 32 accidentally disassembling in a surgical suite.

Figure 11:
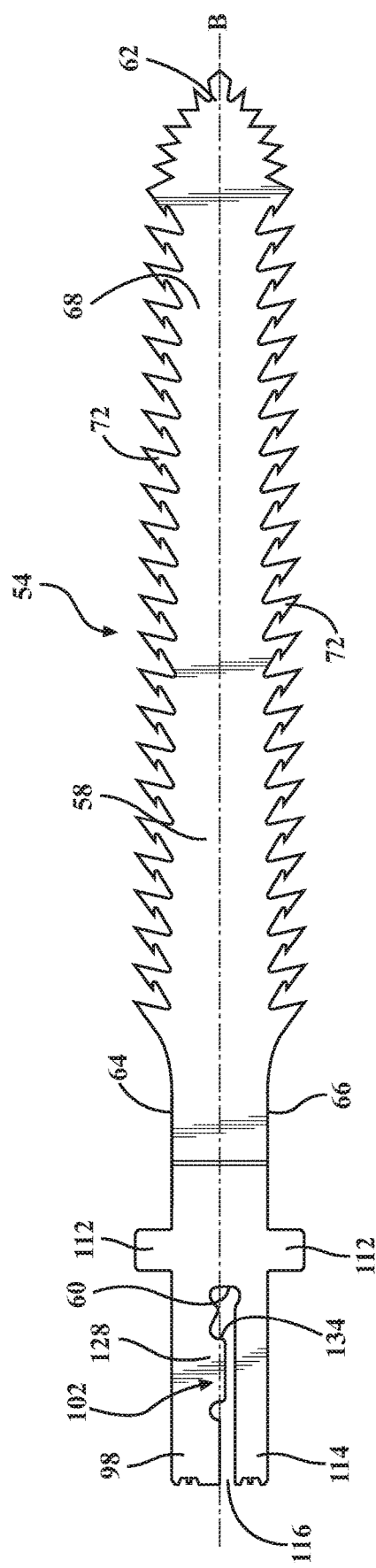
FIG. 11 is an elevation view of another example of a blade of the surgical blade assembly.
Figure 12:
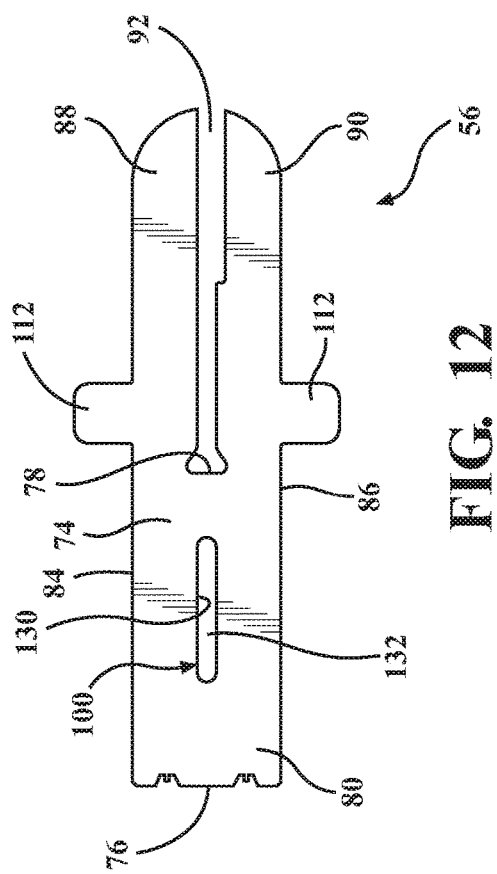
FIG. 12 is a plan view of another example of a reinforcing member of the surgical blade assembly.
Figure 13:
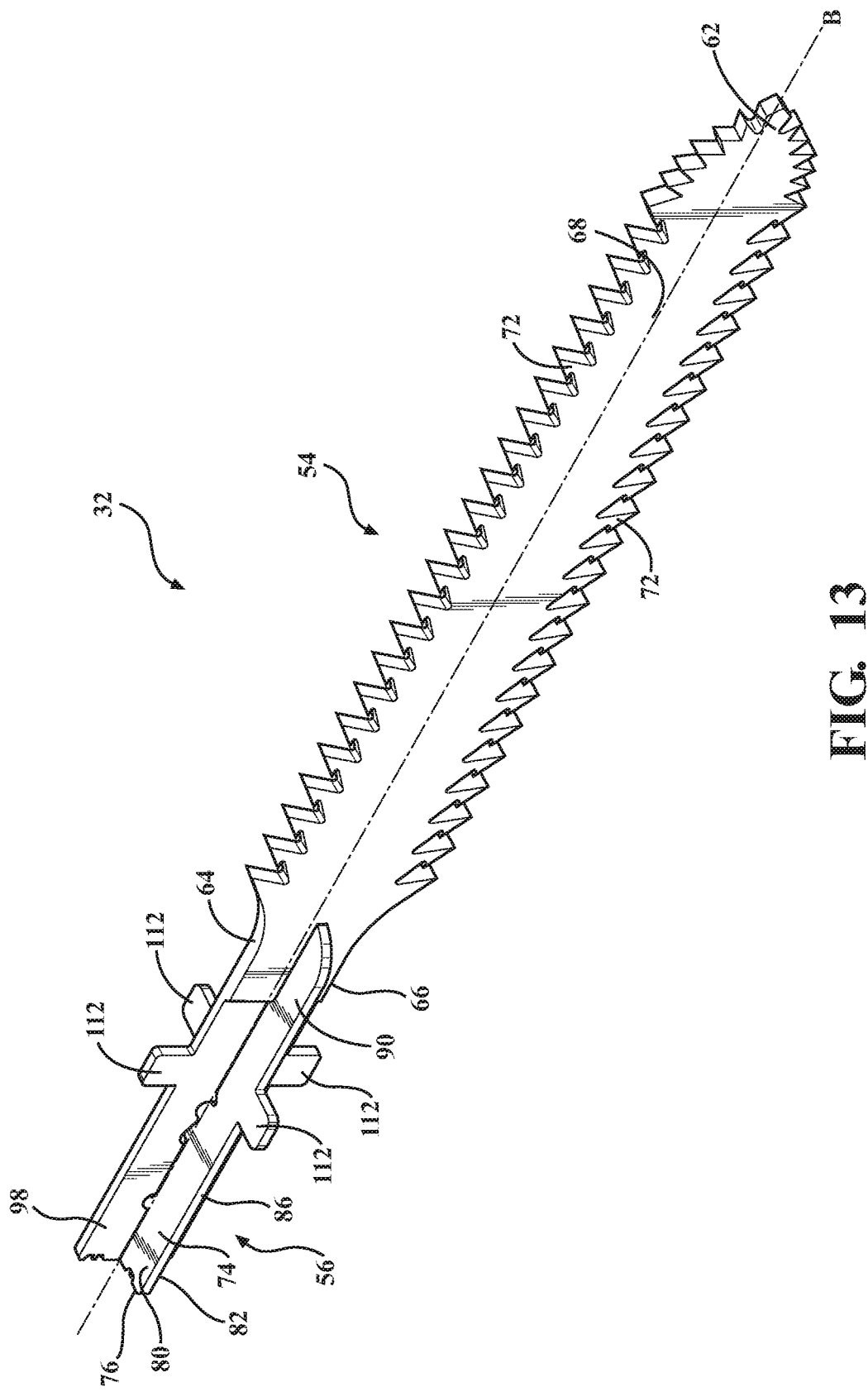
FIG. 13 is a perspective view of another example of the surgical blade assembly with the reinforcing member of FIG. 12 coupled to the blade of FIG. 11.

FIGS. 11-13 show the surgical blade assembly 32 in accordance with another example of the present disclosure. In at least some respects the example shown in FIGS. 11-13 is the same as the examples previously described with like numbers indicating like components. As shown in FIGS. 11-13, the second coupling feature 102 comprises a projection 128 extending from the first leg 98 into the channel 116. The first coupling 100 feature includes a surface 130 of the body portion 74 of the reinforcing member 56. The surface 130 defines a void 132 configured to receive the projection 128 when the receiving portion 92 correspondingly receives the proximal end 60 of the body portion 58 of the blade 54. In this configuration, the surface 130 has a continuous perimeter defining the void 132. In alternative configurations, the surface 130 does not have a continuous perimeter. As shown in FIG. 11, the projection 128 has a stepped portion 134 configured to abut the surface 130 of the reinforcing member 56 that defines the void 132. The abutment between the stepped portion 134 and the surface 130 prevents the reinforcing member 56 from being separated from the blade 54 when the receiving portion 92 receives the proximal end 60 of the body portion 58 of the blade 54. Further, as shown in FIG. 11, the reinforcing member 56 is coupled to the blade 54 by aligning the receiving portion 92 of the reinforcing member 56 with the channel 116 of the blade 54 and pressing the reinforcing member 56 and the blade 54 together. As the receiving portion 92 receives the proximal end 60 of the body portion 58 of the blade 54 and the channel 116 receives the body portion 74 of the reinforcing member 56, the projection 128 abuts the body portion 74 of the reinforcing member 56. One or both of the first and second legs 98, 114 are deflected to create enough space to accommodate the body portion 74 of the reinforcing member 56. Once the reinforcing member 56 and blade 54 have been pressed far enough for the void 132 to receive the projection 128, the abutting surfaces of the stepped portion 134 of the projection 128 and the surface 130 defining the void 132 prevents separation of the reinforcing member 56 from the blade 54. This feature maintains relative axial position between the blade 54 and the reinforcing member 56 and improves handling of the surgical blade assembly 32 without concern for the surgical blade assembly 32 accidentally disassembling in a surgical suite.

Figure 19:
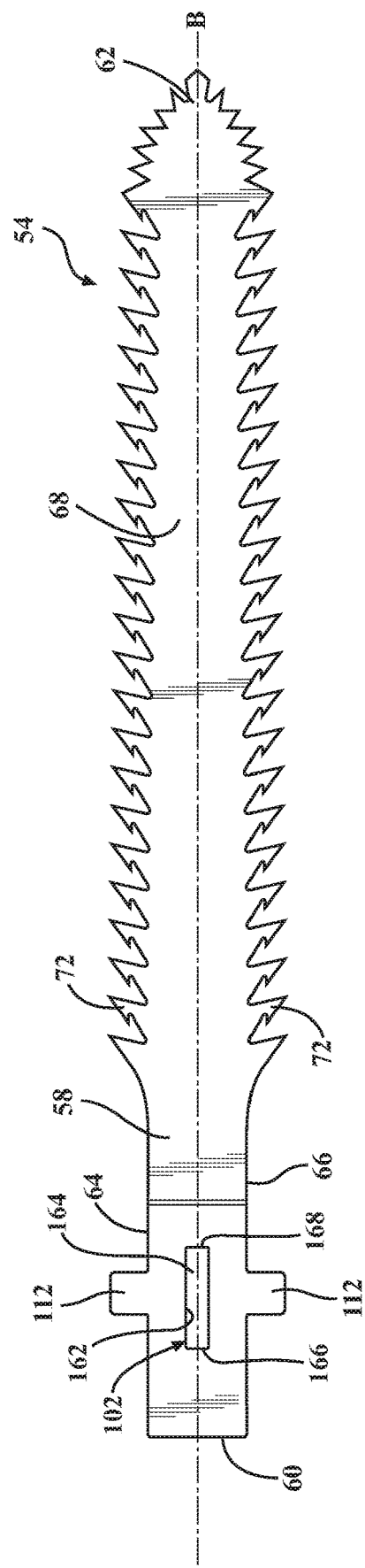
FIG. 19 is an elevation view of another example of a blade of the surgical blade assembly.
Figure 20:
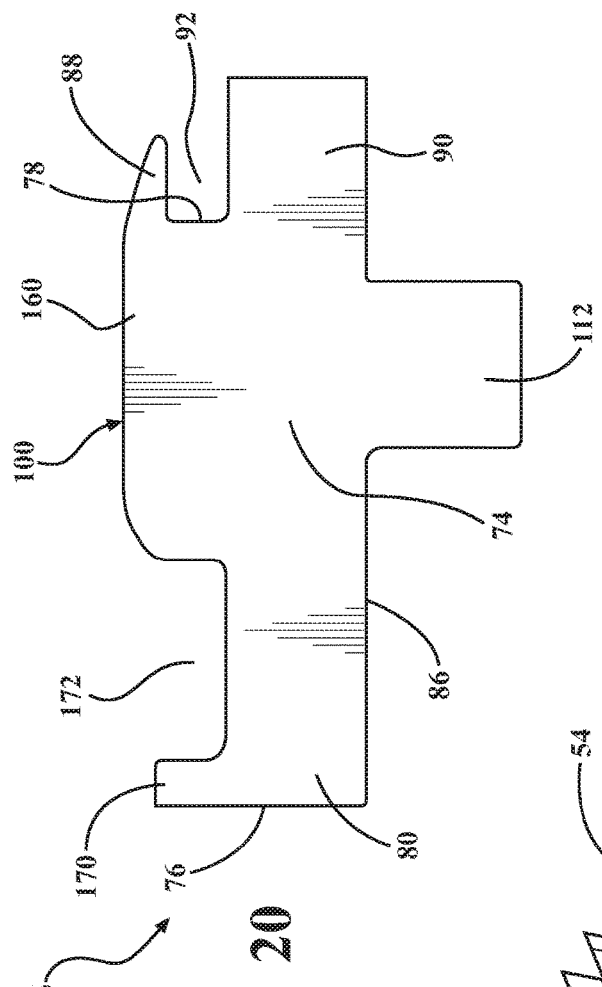
FIG. 20 is a plan view of another example of a reinforcing member of the surgical blade assembly.
Figure 21:
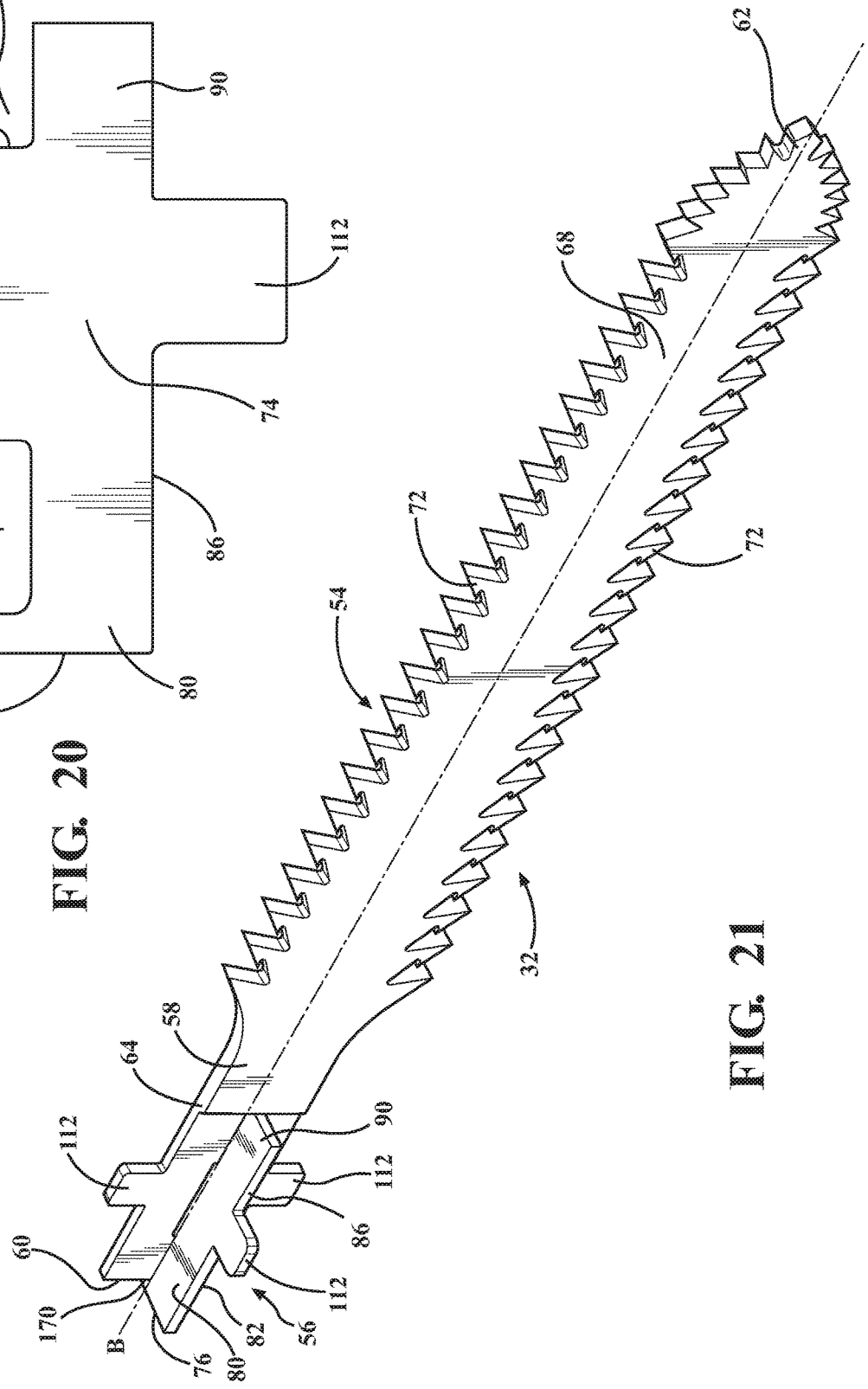
FIG. 21 is a perspective view of another example of the surgical blade assembly with the reinforcing member of FIG. 20 coupled to the blade of FIG. 19.

FIGS. 19-21 show the surgical blade assembly 32 in accordance with another example of the present disclosure. In at least some respects the example shown in FIGS. 19-21 is the same as the example previously described with like numbers indicating like components. As shown in FIGS. 19-21, the first coupling feature 100 includes a projection 160 extending from the body portion 74 of the reinforcing member 56. The second coupling feature 102 has a surface 162 of the body portion 58 of the blade 54 defining a void 164 for receiving the projection 160. Referring to FIG. 19, the surface 162 has a continuous perimeter to define the void 164. The surface 162 of the void 164 defines a first end 166 adjacent to the proximal end 60 of the body portion 58 of the blade 54 and a second end 168 opposite the first end 166 distal to the proximal end 60 of the body portion 58 of the blade 54.

Referring to FIG. 20, the first arm 88 extends from the projection 160 of the body portion 74 of the reinforcing member 56. In the configuration shown, the first arm 88 of the reinforcing member 56 may be shorter than the second arm 90. In other configurations, the first and second arms 88, 90 have identical lengths. The reinforcing member 56 may include a tab 170 extending from the body portion 74 being spaced from the projection 160 to define a groove 172. A length of the groove 172 between the projection 160 and the tab 170 approximates a distance between the proximal end 60 of the body portion 58 of the blade 54 and the first end 166 of the surface 162 defining the void 164.

The reinforcing member 56 is coupled to the blade 54 by feeding the first arm 88 and the projection 160 through the void 164. The receiving portion 92 of the reinforcing member 56 is configured to receive the second end 168 of the surface 162 defining the void 164. The groove 172 is configured to receive a part of the body portion 58 of the blade 54 between the proximal end 60 of the body portion 58 of the blade 54 and the first end 166 of the surface 162 defining the void 164. In some configurations, the projection 160 and the surface 162 defining the void 164 are configured to abut to provide an interference fit to secure the reinforcing member 56 to the blade 54. In other configurations, the tab 170 and the projection 160 abut the proximal end 60 of the body portion 58 of the blade 54 and the first end 166 of the surface 162 defining the void 164, respectively, to provide an interference fit to secure the reinforcing member 56 to the blade 54. In still other configurations, the blade 54 and the reinforcing member 56 each have one or more mount features 112 coupling the blade 54 and the reinforcing member 56 to the saw chuck assembly 40, with the saw chuck assembly 40 constraining the relative position of the reinforcing member 56 to the blade 54.

In the examples described above and shown in FIGS. 2-13 and 19-21, an advantage to the described methods of assembly is that the reinforcing member 56 and the blade 54 are mechanically coupled together without materially altering the physical properties of at least one of the reinforcing member 56 and the blade 54 that may result during a joining process such as welding or brazing. A further advantage is that existing blades may be retrofitted without altering the physical properties, or the like.

Figure 14:
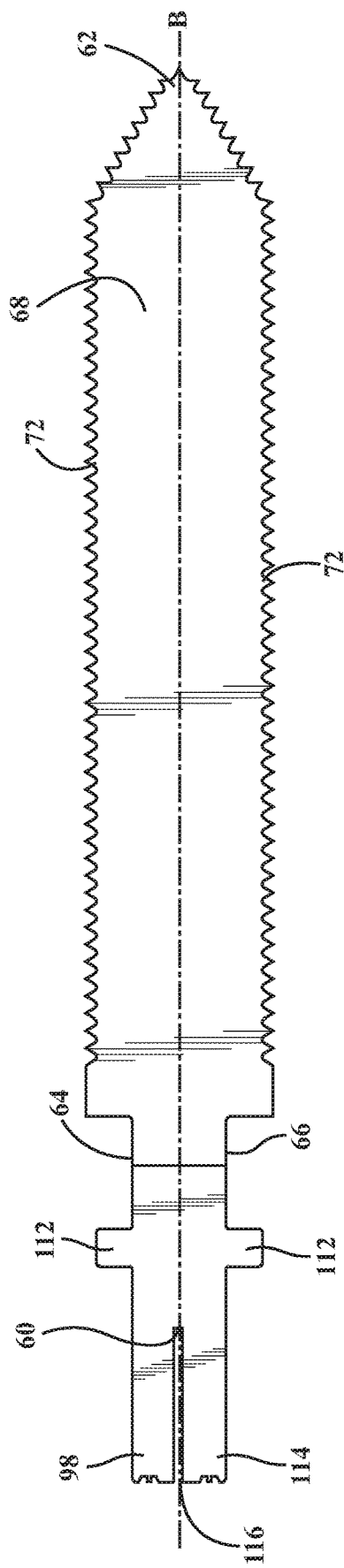
FIG. 14 is an elevation view of another example of a blade of the surgical blade assembly.
Figure 15:
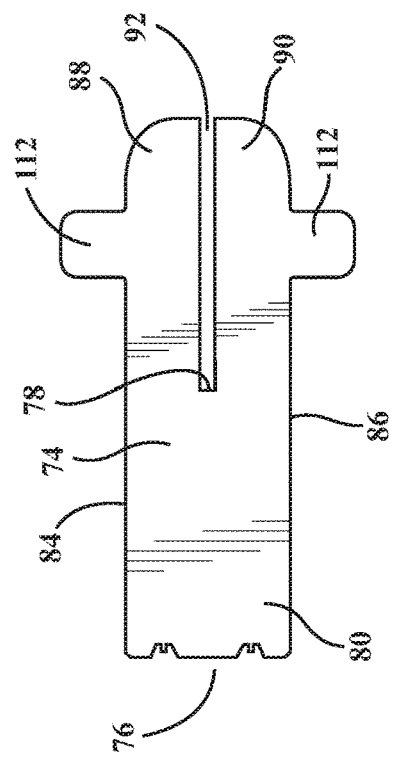
FIG. 15 is a plan view of another example of a reinforcing member of the surgical blade assembly.
Figure 16:
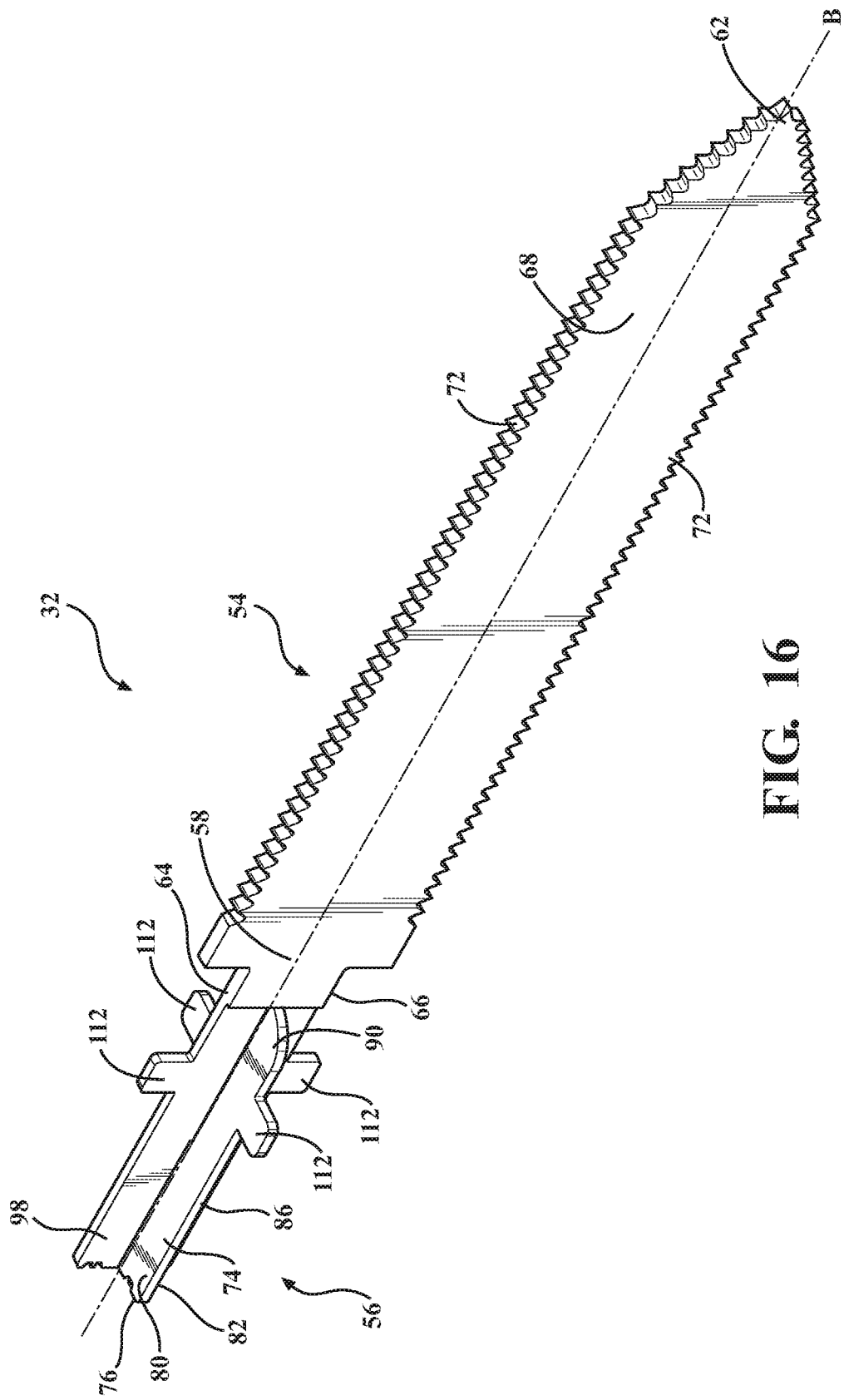
FIG. 16 is a perspective view of another example of the surgical blade assembly with the reinforcing member of FIG. 15 being coupled to the blade of FIG. 14.

FIGS. 14-16 show the surgical blade assembly 32 in accordance with another example of the present disclosure. In at least some respects the example shown in FIGS. 14-16 is the same as the examples previously described with like numbers indicating like components. As shown in FIGS. 14-16, the reinforcing member 56 and blade 54 do not have coupling features. Referring to FIG. 16, the reinforcing member 56 is coupled to the blade 54 by aligning the receiving portion 92 of the reinforcing member 56 with the channel 116 of the blade 54 and pressing the reinforcing member 56 and the blade 54 together. The receiving portion 92 receives the proximal end 60 of the body portion 58 of the blade 54 and the channel 116 correspondingly receives the distal end 78 of the body portion 74 of the reinforcing member 56. In one configuration, an adhesive may be applied to couple the reinforcing member 56 to the blade 54. In another configuration, one or more of the first and second legs 98, 114 and body portion 58 of the blade 54 may be fixed to one or more of the first and second arms 88, 90 and body portion 74 of the reinforcing member 56 by one of welding, brazing, or another process known in the art for permanently joining components together. In another configuration, the blade 54 and the reinforcing member 56 are not fixed together. Instead, the blade 54 and the reinforcing member 56 each have one or more mount features 112 coupling the blade 54 and the reinforcing member 56 to the saw chuck assembly 40, with the saw chuck assembly 40 constraining the relative position of the reinforcing member 56 to the blade 54. The absence of coupling features 100, 102 in the example shown in FIGS. 14-16 results in reduced complexity and low manufacturing costs. This example may also be particularly advantageous with retrofitting an existing blade 54 with the reinforcing member 56.

In the configuration where the reinforcing member 56 is fixed to the blade 54, the reinforcing member 56 may only have one of the first and second arms 88, 90 abutting one of the first and second side surfaces 68, 70 of the body portion 58 of the blade 54 for reinforcing the blade 54. The one of the first and second arms 88, 90 may be fixed to the body portion 58 of the blade 54 and in this manner would reinforce the blade 54 from deflecting toward and away from the one of the first and second arms 88, 90.

Figure 17:
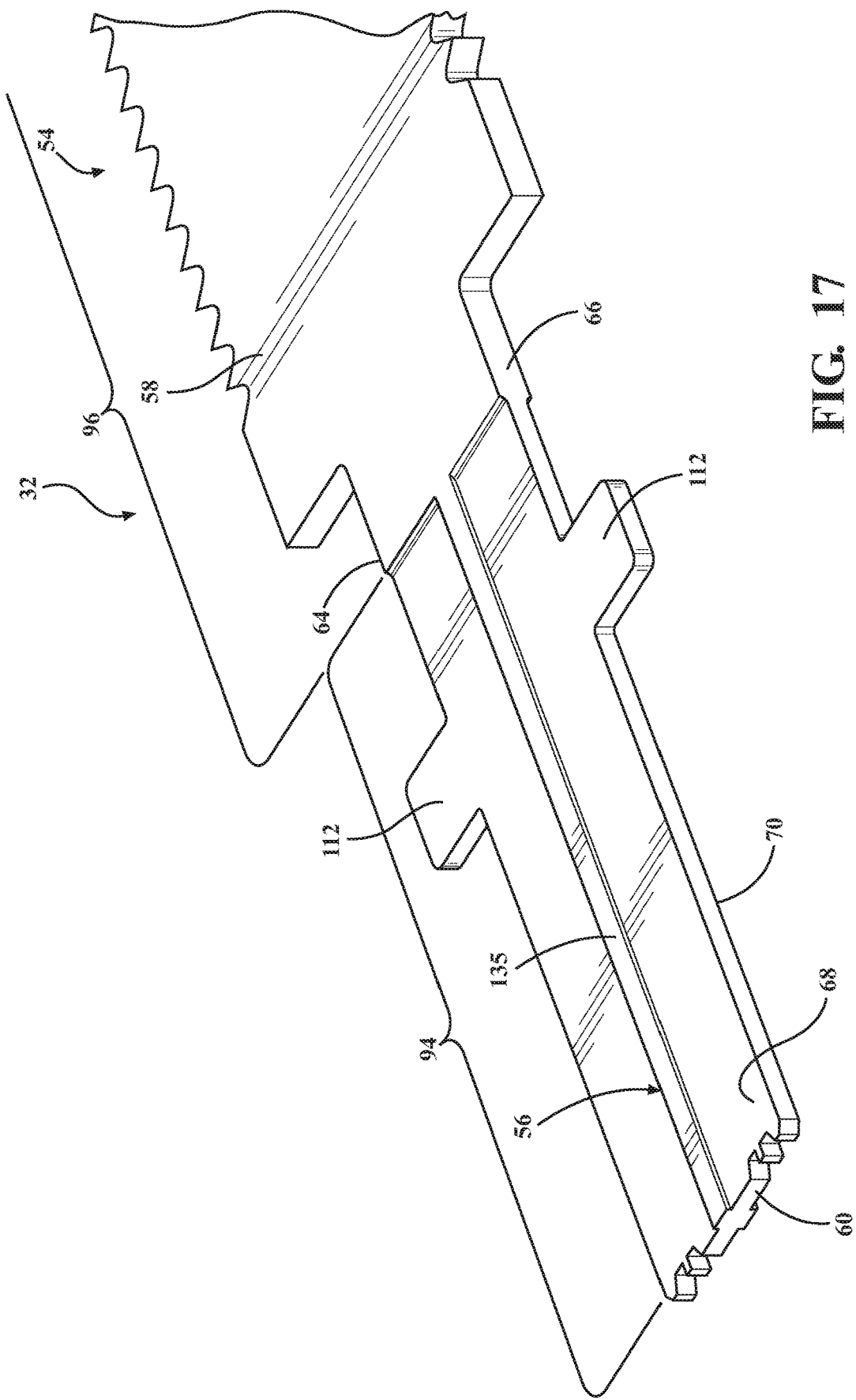
FIG. 17 is a partial perspective view of another example of the surgical blade assembly with the reinforcing member integral with the blade.

In the examples previously described, the reinforcing member 56 is a discrete structure adapted to be coupled to the blade 54. It is also contemplated that the reinforcing member 56 may be integrally formed with the blade 54, as shown in FIG. 17. In one configuration, the reinforcing member 56 comprises a rib 135 that is formed adjacent the proximal end 60 of the body portion 58 of the blade 54. In one configuration shown in FIG. 17, the rib 135 extends from the second region 96 of the body portion 58 of the blade 54 and into the first region 94. The rib 135 extends into the first region 94 at least far enough to be axially closer to the proximal end 60 of the body portion 58 of the blade 54 than the one or more mount features 112. In such a configuration, the rib 135 acts as a strut to reinforce the body portion 58 of the blade 54 from deflecting in directions transverse to the first and second side surfaces 68, 70. The width of the rib 135 may be less than the width of the reinforcing member 56 described above in previous examples. In some examples, the width of the rib 135 is the thickness of the second region of the body portion 58 of the blade 54. In one configuration, the rib 135 may be formed by removing material from the blade 54. In other examples, the rib 135 is formed by stamping or forging.

As previously mentioned, the blade 54 is used to cut tissue, such as bone, during a surgical procedure. The blade 54 may be used to plunge cut involving reciprocating the blade 54 along the blade axis B in manners previously described. To that end, the body portion 58 of the blade 54 has a distal region 136 connecting the top surface 64 and the bottom surface 66 and being disposed between the first and second side surfaces 68, 70. The blade 54 includes one or more teeth 138 that extend outwardly from the distal region 136 of the body portion 58 of the blade 54. The one or more teeth 138 that extend outwardly from the distal region 136 of the body portion 58 of the blade 54 are configured to permit plunge cutting. The one or more teeth 138 that extend outwardly from the distal region 136 generally extend more distally than the one or more teeth 72 along the top and bottom surfaces 64, 66 of the blade 54 to enhance the ability of the blade 54 to penetrate tissue with the distal end 62 of the body portion 58 of the blade 54. In some configurations, at least one tooth 140 of the one or more teeth 138 that extend outwardly from the distal region 136 of the body portion 58 of the blade 54 may extend in a direction substantially aligned with the blade axis B. In one such configuration, the top and bottom surfaces 64, 66 of the body portion 58 of the blade 54 taper toward each other and join at the distal end 62 of the body portion 58 of the blade 54 to form the tooth 140 that is substantially aligned with the blade axis B to permit plunge cutting. In one configuration, the tooth 140 extends at an angle less than thirty degrees relative to the blade axis B. In another configuration, the tooth 140 extends at an angle less than twenty degrees relative to the blade axis B. In other configurations, the tooth 140 extends at an angle less than ten degrees relative to the blade axis B.

Figure 18A:
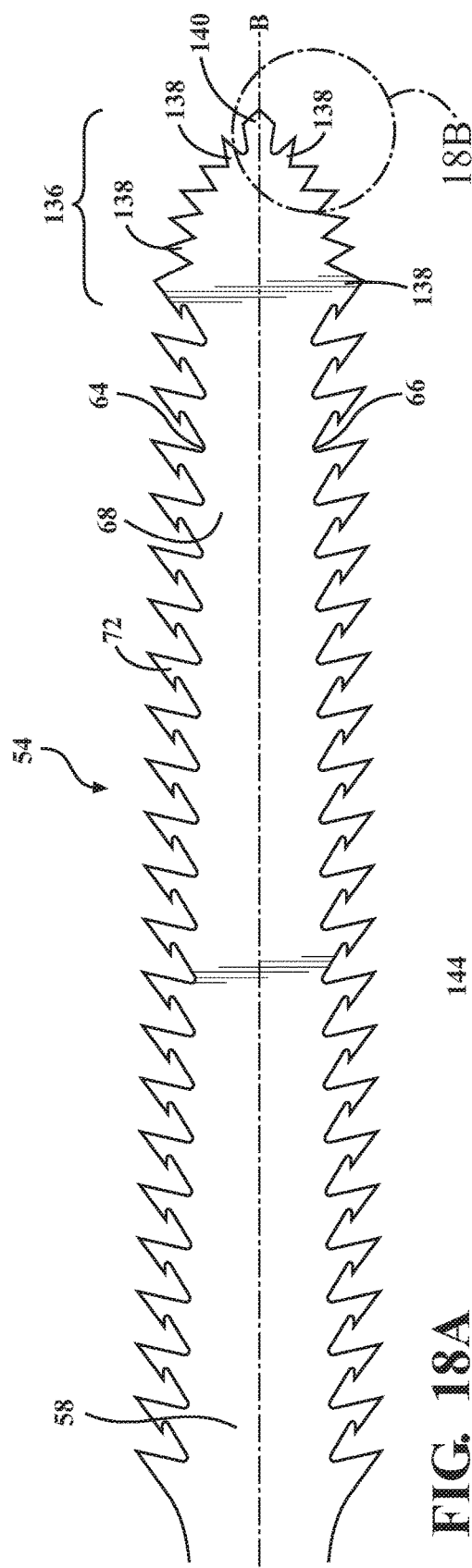
FIG. 18A is an elevation view of teeth extending outwardly from a body portion of the blade of FIG. 2.
Figure 18B:
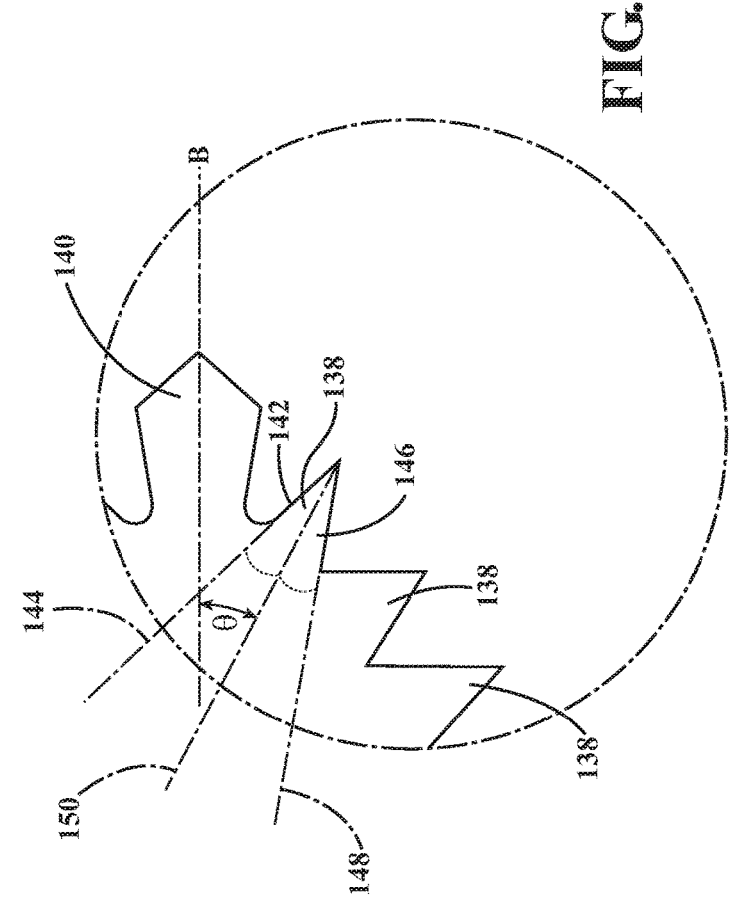
FIG. 18B is a detailed view of a subset of the teeth of FIG. 18A within circle 18B.

In one configuration, as shown in FIGS. 18A and 18B, at least one of the one or more teeth 138 that extend outwardly from the distal region 136 of the body portion 58 of the blade 54 has a tooth face 142 defining a face plane 144. The at least one of the one or more teeth 138 also has a tooth back 146 defining a back plane 148. The face and back planes 144, 148 intersect where the tooth face 142 and the tooth back 146 join together to form a point of the tooth to penetrate tissue. A reference plane 150 bisects the face and back planes 144, 148. An angle θ is created between the reference plane 150 and the blade axis B. In one configuration, the angle θ created between the reference plane 150 and the blade axis B is less than thirty degrees. In other configurations, the angle θ may be less than twenty degrees. In another configuration, the angle θ may be less than ten degrees. In some configurations, one or both the tooth back 146 and the tooth face 142 do not have planar surfaces to define the back plane 148 and face plane 144, respectively. In configurations where the tooth back 146 is not planar, the back plane 148 is defined by a reference plane being tangent to a portion of the surface of the tooth back 146 that is adjacent to the tooth point where the tooth face 142 joins the tooth back 146. In configurations where the tooth face 142 is not planar, the face plane 144 is defined by a reference plane being tangent to a portion of the surface of the tooth face 142 that is adjacent to the tooth point where the tooth face 142 joins the tooth back 146.

In some configurations, as shown in the illustrated examples, the at least one or more teeth 72, 138, 140 extend outwardly from the body portion 58 of the blade 54. The one or more teeth 72, 138, 140 may be coplanar with the thickness of the body portion 58 of the blade 54. More specifically, the side surfaces of the one or more teeth 72, 138, 140 extend substantially parallel to the thickness of the body portion 58 of the blade 54. In other words, the one or more teeth 72, 138, 140 extend substantially parallel to the first and second side surfaces 68, 70 of the body portion 58 of the blade 54. In other configurations, the one or more teeth 72, 138, 140 extend outwardly from the body portion 58 of the blade 54 at an oblique angle relative to the first and second side surfaces 68, 70 of the body portion 58 of the blade 54.

In one configuration, at least one of the blade 54 and the reinforcing member 56 comprises stainless steel. In one configuration the stainless steel comprises martensitic stainless steel. Further the martensitic stainless steel may comprise 7C27Mo2 martensitic stainless steel.

In one configuration, at least one of the blade 54, reinforcing member 56, and features of the blade 54 and reinforcing members 56 are formed by laser cutting.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A surgical blade assembly fora surgical saw, the surgical blade assembly comprising:
a blade comprising a body portion having a proximal end, a distal end, and a length between the proximal and distal ends, with the body portion having opposed top and bottom surfaces and opposed first and second side surfaces between the top and bottom surfaces, and the blade having one or more teeth that extend outwardly from at least one of the top and bottom surfaces of the body portion; and
a reinforcing member comprising a body portion having a proximal end, a distal end, and a length that extends between the proximal and distal ends, the reinforcing member comprising a first arm extending from the distal end of the body portion of the reinforcing member and a second arm extending from the distal end of the body portion of the reinforcing member and being spaced from the first arm to define a receiving portion configured to receive the proximal end of the body portion of the blade,
wherein the first and second arms are configured to abut the first and second side surfaces of the body portion of the blade to act as a strut to reinforce the blade when the receiving portion receives the proximal end of the body portion of the blade; and
wherein the body portion of the blade has a first region adjacent the proximal end of the body portion of the blade and the body portion of the blade has a second region adjacent the first region, with the opposed side surfaces defining a first thickness at the first region of the body portion of the blade and a second thickness larger than the first thickness at the second region of the body portion of the blade.

2. The surgical blade assembly of claim 1, wherein the reinforcing member comprises a first coupling feature and the blade comprises a second coupling feature, with the first and second coupling features configured to engage each other when the receiving portion receives the proximal end of the body portion of the blade to prevent separation of the reinforcing member from the blade.

3. The surgical blade assembly of claim 2, wherein one of the first and second coupling features comprises a projection, and the other of the first and second coupling features comprises a surface defining one of a void and a recess.

4. The surgical blade assembly of claim 2, wherein the blade further comprises a leg extending from the proximal end of the body portion of the blade, the leg being adjacent the body portion of the reinforcing member when the receiving portion receives the proximal end of the body portion of the blade.

5. The surgical blade assembly of claim 4, wherein the body portion of the reinforcing member comprises the first coupling feature and the leg of the blade comprises the second coupling feature.

6. The surgical blade assembly of claim 5, wherein the second coupling feature comprises a projection extending from the leg and the first coupling feature comprises a surface of the body portion of the reinforcing member defining a void to receive the projection when the receiving portion receives the proximal end of the body portion of the blade.

7. The surgical blade assembly of claim 5, wherein the leg is further defined as a first leg and the blade comprises a second leg extending from the proximal end of the body portion and being spaced from the first leg to define a channel configured to receive the distal end of the body portion of the reinforcing member when the receiving portion receives the proximal end of the body portion of the blade.

8. The surgical blade assembly of claim 7, wherein the second coupling feature comprises a projection extending from the first leg into the channel and the first coupling feature comprises a surface of the reinforcing member defining a void to receive the projection when the receiving portion receives the proximal end of the body portion of the blade.

9. The surgical blade assembly of claim 8, wherein the projection has a ramped portion to permit the channel to receive the distal end of the reinforcing member and the projection has a stepped portion configured to abut the surface of the reinforcing member defining the void to prevent the reinforcing member from being separated from the blade when the receiving portion receives the proximal end of the body portion of the blade.

10. The surgical blade assembly of claim 4, wherein at least one of the blade and the reinforcing member comprises a mount feature to releasably attach at least one of the blade and the reinforcing member to the surgical saw.

11. The surgical blade assembly of claim 10, wherein the mount feature comprises a protrusion extending outwardly from at least one of the leg, the body portion of the blade, the first arm, the second arm, and the body portion of the reinforcing member.

12. The surgical blade assembly of claim 1, wherein the body portion of the blade has a distal region connecting the top surface and the bottom surface and disposed between the first and second side surfaces, and the blade having one or more teeth that extend outwardly from the distal region of the body portion of the blade, with the one or more teeth that extend outwardly from the distal region of the body portion of the blade being configured to permit plunge cutting.

13. The surgical blade assembly of claim 12, wherein the length of the body portion of the blade extends along an axis, and at least one of the one or more teeth that extend outwardly from the distal region of the body portion of the blade extends in a direction substantially aligned with the axis.

14. The surgical blade assembly of claim 12, wherein the length of the body portion of the blade extends along an axis, and at least one of the one or more teeth that extend outwardly from the distal region of the body portion of the blade has a tooth face defining a face plane and a tooth back defining a back plane intersecting the face plane, and the at least one of the one or more teeth that extend outwardly from the distal region of the body portion of the blade defines a reference plane bisecting the face and back planes, with the reference plane and the axis creating an angle relative to each other that is less than thirty degrees.

15. The surgical blade assembly of claim 1, wherein the blade and the reinforcing member are perpendicular to each other when the receiving portion receives the proximal end of the body portion of the blade.

16. The surgical blade assembly of claim 1, wherein the receiving portion is adapted to accommodate the second thickness of the body portion of the blade such that the first and second arms abut the first and second side surfaces of the body portion of the blade at the second region of the body portion of the blade when the receiving portion receives the proximal end of the body portion of the blade.

17. The surgical blade assembly of claim 1, wherein at least one of the blade and the reinforcing member comprises stainless steel.

18. The surgical blade assembly of claim 1, wherein the teeth extend outwardly from the body portion of the blade such that the teeth are coplanar with the body portion of the blade.

19. A surgical blade assembly fora surgical saw, the surgical blade assembly comprising:
   a blade comprising a body portion having a proximal end, a distal end, and a length between the proximal and distal ends, with the body portion having opposed top and bottom surfaces and opposed first and second side surfaces between the top and bottom surfaces, and the blade having one or more teeth that extend outwardly from at least one of the top and bottom surfaces of the body portion; and
   a reinforcing member comprising a body portion having a proximal end, a distal end, and a length that extends between the proximal and distal ends, and the reinforcing member comprising a first arm extending from the distal end of the body portion of the reinforcing member and a second arm extending from the distal end of the body portion of the reinforcing member and being spaced from the first arm to define a receiving portion configured to receive the proximal end of the body portion of the blade,
   wherein the first and second arms are configured to abut the first and second side surfaces of the body portion of the blade to act as a strut to reinforce the blade when the receiving portion receives the proximal end of the body portion of the blade; and
   wherein the reinforcing member comprises a first coupling feature and the blade comprises a second coupling feature, with the first and second coupling features configured to engage each other when the receiving portion receives the proximal end of the body portion of the blade to prevent separation of the reinforcing member from the blade;
   wherein the blade further comprises a leg extending from the proximal end of the body portion of the blade, the leg being adjacent the body portion of the reinforcing member when the receiving portion receives the proximal end of the body portion of the blade;
   wherein the second coupling feature comprises a projection extending from the leg and the first coupling feature comprises a surface of the body portion of the reinforcing member defining a void to receive the projection when the receiving portion receives the proximal end of the body portion of the blade.

20. A surgical blade assembly fora surgical saw, the surgical blade assembly comprising:
   a blade comprising a body portion having a proximal end, a distal end, and a length between the proximal and distal ends, with the body portion having opposed top and bottom surfaces and opposed first and second side surfaces between the top and bottom surfaces, and the blade having one or more teeth that extend outwardly from at least one of the top and bottom surfaces of the body portion; and
   a reinforcing member comprising a body portion having a proximal end, a distal end, and a length that extends between the proximal and distal ends, and the reinforcing member comprising a first arm extending from the distal end of the body portion of the reinforcing member and a second arm extending from the distal end of the body portion of the reinforcing member and being spaced from the first arm to define a receiving portion configured to receive the proximal end of the body portion of the blade,
   wherein the first and second arms are configured to abut the first and second side surfaces of the body portion of the blade to act as a strut to reinforce the blade when the receiving portion receives the proximal end of the body portion of the blade; and
   wherein the blade further comprises a leg extending from the proximal end of the body portion of the blade, the leg being adjacent the body portion of the reinforcing member when the receiving portion receives the proximal end of the body portion of the blade;
   wherein the leg is further defined as a first leg and the blade comprises a second leg extending from the proximal end of the body portion and being spaced from the first leg to define a channel configured to receive the distal end of the body portion of the reinforcing member when the receiving portion receives the proximal end of the body portion of the blade.

* * * * *